US00PP10306P

United States Patent [19]

Kientzler

[11] Patent Number: Plant 10,306

[45] Date of Patent: Mar. 24, 1998

[54] NEW GUINEA IMPATIENS PLANT NAMED 'TORTOLA'

[75] Inventor: Ludwig Kientzler, Gensingen, Germany

[73] Assignee: Paul Ecke Ranch, Inc., Encinitas, Calif.

[21] Appl. No.: 780,698

[22] Filed: Jan. 8, 1997

[51] Int. Cl.[6] ..... A01H 5/00

[52] U.S. Cl. ..... Plt./87.6

[58] Field of Search ..... Plt./87.6

*Primary Examiner*—James R. Feyrer

*Attorney, Agent, or Firm*—C. A. Whealy

[57] ABSTRACT

A new and distinct cultivar of New Guinea Impatiens plant named 'Tortola', characterized by its flat and rounded light pink-colored flowers; outwardly spreading, mounded and compact growth habit; and dark green, somewhat glossy, non-variegated foliage.

1 Drawing Sheet

The present invention relates to a new and distinct cultivar of New Guinea Impatiens plant, botanically known as *Impatiens hawkeri*, known by the name 'Kitort', and hereinafter referred to by the cultivar name 'Tortola'.

The new cultivar is a product of a planned breeding program conducted by the inventor in Gensingen, Germany. The objective of the breeding program was to develop new varieties that have a uniform plant habit, attractive flower colors, good flower form and numerous flowers per plant.

The new cultivar originated from a cross made by the inventor of a proprietary seedling selection identified as S837 as the male, or pollen parent, with the proprietary seedling selection identified as W354 as the female, or seed patent. The cultivar 'Tortola' was discovered and selected by the inventor as a flowering plant within the progeny of the stated cross in a controlled environment in Gensingen, Germany. Asexual reproduction of the new cultivar by terminal cuttings taken at Gensingen, Germany, has shown that the unique features of this new Impatiens are stable and reproduced true to type in successive generations of asexual reproduction.

The following traits have been repeatedly observed and are determined to be the unique characteristics of 'Tortola'. These characteristics in combination distinguish 'Tortola' as a new and distinct cultivar:

1. Flat and rounded light pink-colored flowers.
2. Outwardly spreading, mounded and compact growth habit.
3. Dark green, somewhat glossy, non-variegated foliage.

The new New Guinea Impatiens is similar in flower color to the New Guinea Impatiens cultivar 'Light Pink' (U.S. plant pat. applied for). However in side-by-side comparisons in Encinitas, Calif., under commercial practice, plants of the new New Guinea Impatiens differed from plants of the cultivar 'Light Pink' in the following characteristics:

1. Plants of the new New Guinea Impatiens are less upright and more outwardly spreading and denser than plants of the cultivar 'Light Pink'.
2. Plants of the new New Guinea Impatiens are more compact than plants of the cultivar 'Light Pink'.
3. Plants of the new New Guinea Impatiens have thicker and redder stems than plants of the cultivar 'Light Pink'.
4. Lower venation color of leaves of plants of the new New Guinea Impatiens is redder than lower venation color of leaves of plants of the cultivar 'Light Pink'.
5. Flower spurs of plants of the new New Guinea Impatiens are dark purple in color whereas flower spurs of plants of the cultivar 'Light Pink' are pink in color.

6. Peduncles of plants of the new New Guinea Impatiens are longer and redder than peduncles of plants of the cultivar 'Light Pink'.

A detailed comparison of plants of the new New Guinea Impatiens and the cultivar 'Light Pink' appears in Chart A at the end of the specification.

The accompanying colored photographs illustrate the overall appearance of the new cultivar, showing the colors as true as it is reasonably possible to obtain in colored reproductions of this type.

The first photograph comprises a top perspective view of a typical plant of 'Tortola'.

The second photograph comprises a close-up view of typical flowers and upper (left) and lower (right) surfaces of leaves of the cultivars 'Light Pink' (top of photo) and 'Tortola' (bottom of photo).

Flower and foliage colors in the photographs may 'differ' from the actual colors due to light reflectance.

The cultivar 'Tortola' has not been observed under all possible environmental conditions. The phenotype may vary somewhat with variations in environment such as temperature and light intensity, without, however, any variance in genotype. The following observations, measurements and comparisons describe plants grown 10-cm pots in Encinitas, Calif., under commercial practice in a fiberglass-covered greenhouse with day temperatures ranging from 23 to 29C. and night temperatures ranging from 16 to 18C. and about 3,000 footcandles.

In the following description, color references are made to The Royal Horticultural Society Colour Chart except where general terms of ordinary dictionary significance are used.

Classification:

*Botanical.*—*Impatiens hawkeri* 'Tortola'.

*Commercial.*—New Guinea Impatiens cv. 'Tortola'.

Parentage:

*Male parent.*—Proprietary seedling selection S837.

*Female parent.*—Proprietary seedling selection W354.

Propagation:

*Type cutting.*—Terminal cuttings.

*Time to intiate roots.*—About 15 days with 21C soil temperature.

Plant description:

*Plant form.*—Outwardly spreading, mounded and compact.

*Growth habit.*—Moderately vigorous. Suitable for 10 to 25-cm containers.

*plant size.*—Height: About 18 cm. Width or spread: About 22 cm.

*Lateral branches.*—Quantity: About five. Size: Length: 13 to 14 cm. Diameter: 1 to 1.2 cm. Internode length: About 4 cm. Color: 59A/60B.

*Foliage description.*—Leaves simple, generally symmetrical, abundant, opposite or in whorls of three, horizontal to plant and flat in aspect. Size, largest leaves: Length: 11 to 12 cm. Width: 4 to 4.3 cm. Shape: Ovate with acuminate apex, attenuate base and ciliate margin. Texture: Smooth, somewhat glossy. Color: Young foliage, upper surface: 146A. Young foliage, lower surface: 147C. Fully expanded foliage, upper surface: 147A. Fully expanded foliage, lower surface: 147B. Venation, upper surface: 60C. Venation, lower surface: 60B. Petiole: Size: Length: About 4 cm. Diameter: About 4 mm. Color: 60B/60C.

Flower Description:

*Flower type and habit.*—Light pink-colored flowers. Freely and continuously flowering. Flowers arise from leaf axils. Usually seven to eight flowers per lateral branch. Flowers positioned above the foliage and face mostly upward and some, outward. Flowers flat and rounded triangular, somewhat triangular. Flowers persistent.

*Flowering season.*—Year-round under greenhouse conditions. In the garden, flowering is continuous from spring until fall.

*Flower size.*—Length: 5.5 to 6 cm. Width: 5.5 to 6 cm. Depth: About 5 mm.

*Flower buds.*—Size: Length: About 2.5 cm. Diameter: About 1.5 cm. Shape: Ovoid. Color: 55A/52C.

*Petals.*—Quantity: Five. Shape: Cordate with emarginate apex, cuneate or obtuse base and entire margin. Texture: Smooth. Color: When opening, upper surface: Iridescent, 52C. When opening, lower surface: Iridescent, 52D. Fully opened, upper surface: Iridescent, 55C/55D, white towards center with 64C at petal base. Fully opened, lower surface: Iridescent, 55C. Fading to: 55C.

*Spur.*—Length: About 4.7 cm. Shape: Narrow and curved. Color: 59A/60A.

*Peduncles.*—Length: 5.3 to 5.5 cm. Angle: Mostly erect, some outward. Strength: Strong. Color: 60A.

*Reproductive organs.*—Androecium: Stamen number: Five, anthers fused, filaments free. Anther shape: Obovate. Anther size: 6 by 4 mm. Anther color: Cream. Amount of pollen: Moderate. Pollen color: Cream. Gynoecium: Five-loculate fused. Gynoecium length: About 6 mm. Gynoecium color: 146A.

Disease resistance: Under commercial conditions, resistance nor susceptibility to pathogens has not been observed.

Seed development: Seed production is not usually observed.

CHART A

| CHARACTERISTIC | 'TORTOLA' | 'LIGHT PINK' |
|---|---|---|
| GROWTH HABIT | Upright to outwardly spreading and mounding, compact | Upright, somewhat open |
| PLANT HEIGHT | About 18 cm | About 22 cm |
| PLANT WIDTH | About 22 cm | About 26 cm |
| LATERAL BRANCH DIAMETER | 1 to 1.2 cm | About 6 mm |
| INTERNODE LENGTH | About 4 cm | About 6 cm |
| STEM COLOR | 59A/60B | 146C |
| LEAF VENATION COLOR, UPPER SURFACE | 60C | 59D |
| LEAF VENATION COLOR, LOWER SURFACE | 60B | 146D with stripes of 59B |
| PETIOLE LENGTH | About 4 cm | 2.5 to 3 cm |
| PETIOLE DIAMETER | About 4 mm | About 5 mm |
| PETIOLE COLOR | 60B/60C | 63B |
| PETAL COLOR, WHEN OPENING, UPPER SURFACE | 52C | 55B |
| PETAL COLOR, WHEN OPENING, LOWER SURFACE | 52D | 55C |
| PETAL COLOR, OPENED, UPPER SURFACE | 55C/55D with white towards center and 64C at petal base | 55B with white towards center and 68A/68B at petal base |
| PETAL COLOR, OPENED, LOWER SURFACE | 55C | 55C |
| PETAL COLOR FADING TO | 55C | 55D to white |
| SPUR LENGTH | About 4.7 cm | 5 to 5.5 cm |
| SPUR COLOR | 59A/60A | 51A/51C |
| PEDUNCLE LENGTH | 5.3 to 5.5 cm | 4.3 to 4.8 cm |
| PEDUNCLE COLOR | 60A | 144B |
| FLOWER BUD COLOR | 55A/52C | 55A/55B |

It is claimed:

1. A new and distinct cultivar of New Guinea Impatiens plant named 'Tortola', as illustrated and described.

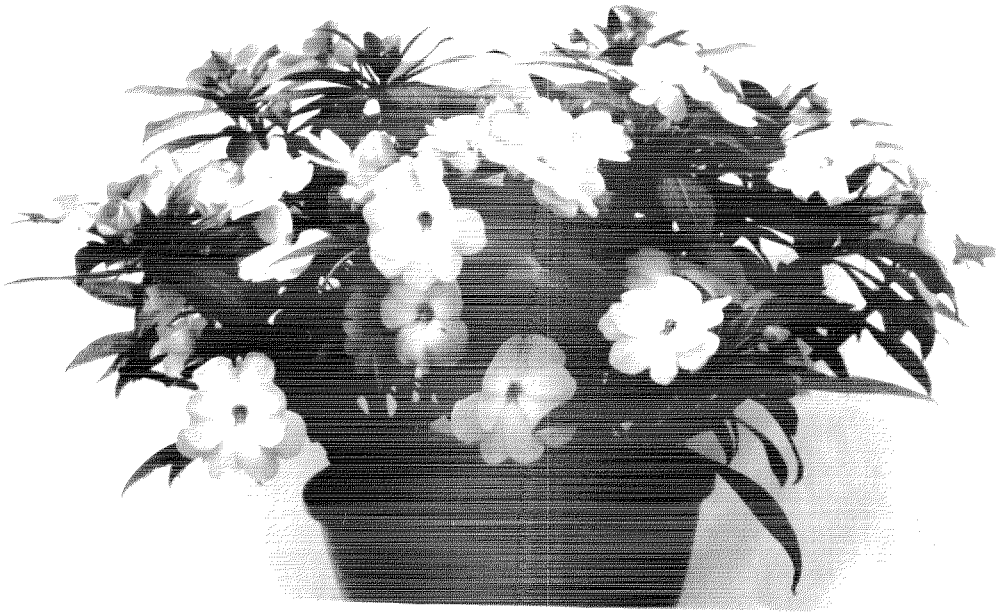
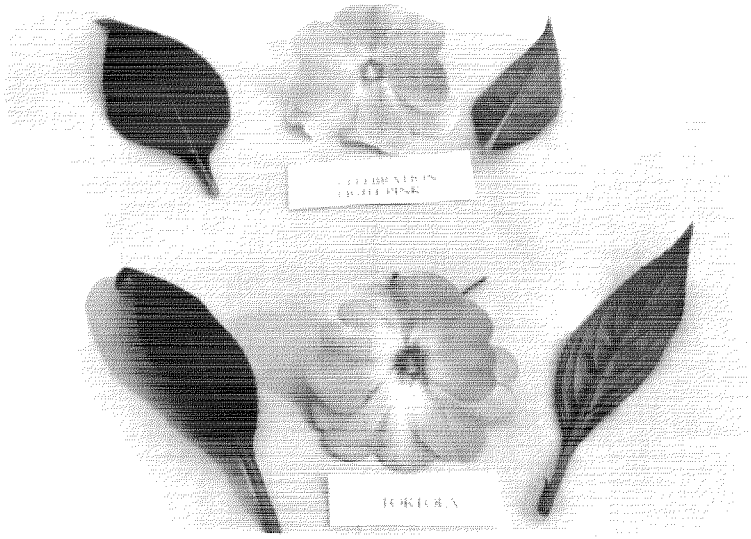

* * * * *